(12) United States Patent
Odaka et al.

(10) Patent No.: US 6,677,363 B1
(45) Date of Patent: Jan. 13, 2004

(54) AGENT FOR IMPROVING KETOSIS

(75) Inventors: Hiroyuki Odaka, Kobe (JP); Masami Suzuki, Ikeda (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/937,447

(22) PCT Filed: Apr. 13, 2000

(86) PCT No.: PCT/JP00/02413

§ 371 (c)(1),
(2), (4) Date: Sep. 26, 2001

(87) PCT Pub. No.: WO00/61127

PCT Pub. Date: Oct. 19, 2000

(30) Foreign Application Priority Data

Apr. 14, 1999 (JP) .......................................... 11/107119

(51) Int. Cl.⁷ ........................ A61K 31/425; A61K 38/28
(52) U.S. Cl. ........................................... 514/369; 514/3
(58) Field of Search ..................................... 514/3, 369

(56) References Cited

U.S. PATENT DOCUMENTS

| | | | | |
|---|---|---|---|---|
| 5,932,601 A | * | 8/1999 | Sohda et al. ................. | 514/376 |
| 5,965,589 A | * | 10/1999 | Sohda et al. ................. | 514/369 |
| 6,251,926 B1 | * | 6/2001 | Momose et al. ............. | 514/364 |
| 6,329,403 B1 | * | 12/2001 | Odaka et al. ................ | 514/342 |
| 2002/0042441 A1 | * | 4/2002 | Acton, III et al. .......... | 514/415 |

FOREIGN PATENT DOCUMENTS

| | | |
|---|---|---|
| EP | 0 749 751 A2 | 12/1996 |
| WO | WO 97/37656 | 10/1997 |
| WO | WO 98/57634 | 12/1998 |

OTHER PUBLICATIONS

Windholz et al., The Merck Index, Tenth Edition (1983) pp. 723 and 724, abstract No. 4866.*

Inoue, I. et al. "Effect of Troglitazone (CS–045) and benzafibrate on glucose tolerance, liver glycogen synthase activity, and beta–oxidation in fructose–fed rats." Metabolism Clinical and Experimental vol. 44(12):1626–1630 (1995).

Kemnitz, J. et al. "Pioglitazone increases insulin sensitivity, reduces blood glucose, insulin, and lipid levels and lowers blood pressure in obese, insulin–resistant rhesus monkeys." Diabetes vo. 43(2):204–211 (1994).

Fujiwara, T. "Characterization of new oral antidiabetic agent CS–045 studies in KK and OB–OB mice Zucker fatty rats." Diabetes vol. 37(11):1549–1558 (1988).

Murakami, K. et al. "A novel insulin sensitizer acts as a coligand for peroxisome proliferator–activated receptor–alpha (PPAR–alpha) and PPAR–gamma. Effect of PPAR–alpha activation on abnormal lipid metabolism in liver of Zucker fatty rats." Diabetes vol. 47(12):1841–1847 (1998).

Oakes, N. et al. "A new antidiabetic agent BRL 49653, reduces lipid availability and improves insulin action and glucoregulation in the rat." Diabetes vol. 43(10):1203–1210 (1994).

Bowen, L. et al. "The effect of CP–68722 A Thiozolidinedione derivative on insulin sensitivity in lean and obese Zucker rats." Metabolism Clinical and Experimental vol. 40(10):1025–1030 (1991).

* cited by examiner

*Primary Examiner*—Kevin E. Weddington
(74) *Attorney, Agent, or Firm*—Mark Chao; Elaine M. Ramesh

(57) ABSTRACT

An agent for improving ketosis which comprises an insulin sensitizer, which has an excellent action and low toxicity.

16 Claims, No Drawings

AGENT FOR IMPROVING KETOSIS

This application is the National Phase filing of International Patent Application No. PCT/JP00/02413, filed Apr. 13, 2000.

TECHNICAL FIELD

The present invention relates to an agent for improving (ameliorating or treating) ketosis which comprises an insulin sensitizer (insulin resistance-improving agent).

Also, the present invention relates to an agent for improving (ameliorating or treating) acidosis which comprises an insulin sensitizer.

Further, the present invention relates to an agent for preventing or treating hyperosmolar nonketonic coma, infectious disease, diabetic osteoporosis, diabetic gangrene, xerostomia, lowered sense of hearing, angina pectoris, cerebrovascular disease or peripheral circulatory disturbance, which comprises an insulin sensitizer.

BACKGROUND ART

Ketosis is a condition in which a large amount of ketone bodies are accumulated in tissue and body fluids because of enhanced production of ketone bodies exceeding the body's ability to utilize them. An increase in the concentration of hydrogen ions released by the ketone bodies is known to cause acidosis.

Acidosis is a condition in which the acid-base balance of body fluids, especially blood is skewed to the acid side. Serious acidosis is known to cause disturbance of consciousness or coma.

An insulin sensitizer is also called an insulin sensitivity enhancer, and is employed as an anti-diabetic agent, if necessary in combination with other anti-diabetic agents.

JP-A H9(1997)-67271 describes "a pharmaceutical composition which comprises an insulin sensitivity enhancer in combination with at least one member selected from the group consisting of α-glucosidase inhibitor, an aldose reductase inhibitor, a biguanide, a statin compound, a squalene synthesis inhibitor, a fibrate compound, a LDL catabolism enhancer and an angiotensin converting enzyme inhibitor".

WO 98/57634 describes "a method for the treatment of diabetes mellitus and conditions associated with diabetes mellitus in a mammal, which method comprises administering an effective non-toxic and pharmaceutically acceptable amount of an insulin sensitiser and a biguanide antihyperglycaemic agent, to a mammal in need thereof".

An insulin sensitizer is also known to be useful as an agent for the prophylaxis and treatment of cachexia (WO 97/37656).

However, there has been no report that an insulin sensitizer is useful as an agent for improving ketosis or an agent for improving acidosis.

Development of an agent for improving ketosis with excellent action and low toxicity is desired.

Further, an agent for improving acidosis with excellent action and low toxicity is also desired.

DISCLOSURE OF INVENTION

The present invention relates to
(1) an agent for improving ketosis which comprises an insulin sensitizer;
(2) an agent according to the above (1), wherein the insulin sensitizer is a compound of the formula:

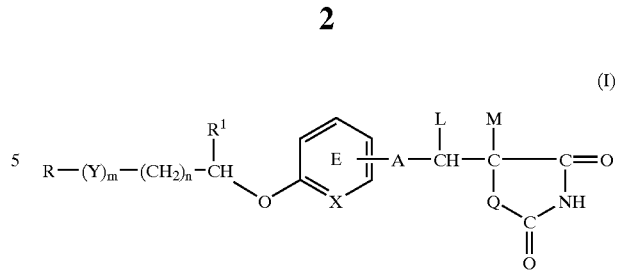

wherein R represents a hydrocarbon group that may be substituted or a heterocyclic group that may be substituted; Y represents a group of the formula —CO—, —CH(OH)—, or —$NR^3$— where $R^3$ represents an alkyl group that may be substituted; m is 0 or 1; n is 0, 1 or 2; X represents CH or N; A represents a chemical bond or a bivalent aliphatic hydrocarbon group having 1 to 7 carbon atoms; Q represents oxygen or sulfur; $R^1$ represents hydrogen or an alkyl group; ring E may have further 1 to 4 substituents, which may form a ring in combination with $R^1$; L and M respectively represent hydrogen or may be combined with each other to form a chemical bond; or a salt thereof;
(3) an agent according to the above (1), wherein the insulin sensitizer is pioglitazone hydrochloride, troglitazone, rosiglitazone, 4-[4-[2-(5-methyl-2-phenyloxazol-4-yl) ethoxy]benzyl]isoxazolidin-3,5-dione or 5-[[6-(2-fluorobenzyloxy)-2-naphthyl]methyl]-2,4-thiazolidinedione;
(4) an agent according to the above (1), wherein the ketosis is diabetic ketosis;
(5) an agent according to the above (1), wherein the ketosis is ketosis caused by a biguanide;
(6) an agent according to the above (1), which is an agent for preventing or treating hepatic glycogenosis, endocrine diseases, congenital metabolic disorders of carbohydrates or organic acids, acetonemia vomiting or gastrointestinal diseases;
(7) an agent for improving acidosis which comprises an insulin sensitizer;
(8) an agent according to the above (7), wherein the insulin sensitizer is a compound of the formula:

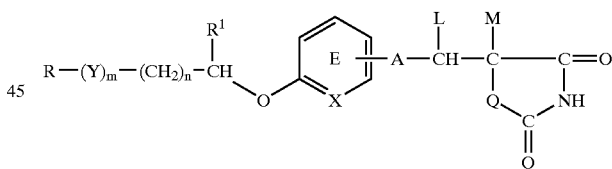

wherein R represents a hydrocarbon group that may be substituted or a heterocyclic group that may be substituted; Y represents a group of the formula —CO—, —CH(OH)—, or —$NR^3$— where $R^3$ represents an alkyl group that may be substituted; m is 0 or 1; n is 0, 1 or 2; X represents CH or N; A represents a chemical bond or a bivalent aliphatic hydrocarbon group having 1 to 7 carbon atoms; Q represents oxygen or sulfur; $R^1$ represents hydrogen or an alkyl group; ring E may have further 1 to 4 substituents, which may form a ring in combination with $R^1$; L and M respectively represent hydrogen or may be combined with each other to form a chemical bond; or a salt thereof;
(9) an agent according to the above (7), wherein the insulin sensitizer is pioglitazone hydrochloride, troglitazone, rosiglitazone, 4-[4-[2-(5-methyl-2-phenyloxazol-4-yl) ethoxy]benzyl]isoxazolidin-3,5-dione or 5-[[6-(2-fluorobenzyloxy)-2-naphthyl]methyl]-2,4-thiazolidinedione;

(10) an agent according to the above (7), wherein the acidosis is diabetic acidosis;

(11) an agent according to the above (7), wherein the acidosis is acidosis caused by a biguanide;

(12) an agent according to the above (7), which is an agent for preventing or treating disturbance of consciousness, coma or respiratory diseases;

(13) an agent for preventing or treating hyperosmolar nonketonic coma, infectious disease, diabetic osteoporosis, diabetic gangrene, xerostomia, lowered sense of hearing, angina pectoris, cerebrovascular disease or peripheral circulatory disturbance, which comprises an insulin sensitizer;

(14) an agent according to the above (13), wherein the insulin sensitizer is pioglitazone hydrochloride, troglitazone, rosiglitazone, 4-[4-[2-(5-methyl-2-phenyloxazol-4-yl)ethoxy]benzyl]isoxazolidin-3,5-dione or 5-[[6-(2-fluorobenzyloxy)-2-naphthyl]methyl]-2,4-thiazolidinedione;

(15) an agent for improving ketosis which comprises an insulin sensitizer in combination with insulin;

(16) an agent for improving acidosis which comprises an insulin sensitizer in combination with insulin;

(17) method for improving or treating ketosis in a mammal in need thereof, which comprises administering to said mammal an effective amount of an insulin sensitizer;

(18) method for improving or treating acidosis in a mammal in need thereof, which comprises administering to said mammal an effective amount of an insulin sensitizer;

(19) method for preventing or treating hyperosmolar nonketoniccoma, infectious disease, diabetic osteoporosis, diabetic gangrene, xerostomia, lowered sense of hearing, angina pectoris, cerebrovascular disease or peripheral circulatory disturbance in a mammal in need thereof, which comprises administering to said mammal an effective amount of an insulin sensitizer;

(20) use of an insulin sensitizer for the manufacture of a pharmaceutical preparation for improving or treating ketosis;

(21) use of an insulin sensitizer for the manufacture of a pharmaceutical preparation for improving or treating acidosis; and

(22) use of an insulin sensitizer for the manufacture of a pharmaceutical preparation for treating hyperosmolar nonketonic coma, infectious disease, diabetic osteoporosis, diabetic gangrene, xerostomia, lowered sense of hearing, angina pectoris, cerebrovascular disease or peripheral circulatory disturbance.

The insulin sensitizer used in the present invention means any and all drugs that restore the impaired insulin receptor function and improve insulin resistance. Specific examples of the insulin sensitizer include the above-mentioned compound represented by the formula (I) or a salt thereof.

Referring to the formula (I), examples of the hydrocarbon group in the hydrocarbon group that may be substituted for R include aliphatic hydrocarbon groups, alicyclic hydrocarbon groups, alicyclic-aliphatic hydrocarbon groups, aromatic-aliphatic hydrocarbon groups, and aromatic hydrocarbon groups. The number of carbon atoms constituting such hydrocarbon groups is preferably 1 to 14.

The aliphatic hydrocarbon group is preferably a $C_{1-8}$ aliphatic hydrocarbon group. Examples of the aliphatic hydrocarbon group includes saturated $C_{1-8}$ aliphatic hydrocarbon groups (e.g. alkyl groups, etc.) such as methyl, ethyl, propyl, isopropyl, butyl, isobutyl, sec-butyl, t-butyl, pentyl, isopentyl, neopentyl, t-pentyl, hexyl, isohexyl, heptyl, and octyl; and unsaturated $C_{2-8}$ aliphatic hydrocarbon groups (e.g. alkenyl groups, alkadienyl groups, alkynyl groups, alkadiynyl groups, etc.) such as vinyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl.

The alicyclic hydrocarbon group is preferably a $C_{3-7}$ alicyclic hydrocarbon group. Examples of the alicyclic hydrocarbon group include saturated $C_{3-7}$ alicyclic hydrocarbon groups (e.g. cycloalkyl groups, etc.) such as cyclopropyl, cyclobutyl, cyclopentyl, cyclohexyl, cycloheptyl, etc. and unsaturated $C_{5-7}$ alicyclic hydrocarbon groups (e.g. cycloalkenyl groups, cycloalkadienyl groups, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, and 2,4-cycloheptadienyl.

The alicyclic-aliphatic hydrocarbon group is a group consisting of the above-described alicyclic hydrocarbon group and aliphatic hydrocarbon group (e.g. cycloalkyl-alkyl groups, cycloalkenyl-alkyl groups, etc.) and is preferably a $C_{4-9}$ alidyclic-aliphatic hydrocarbon group. Examples of the alicyclic-aliphatic hydrocarbon group include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, etc.

The aromatic-aliphatic hydrocarbon group is preferably a $C_{7-13}$ aromatic-aliphatic hydrocarbon group (e.g. aralkyl groups, etc.). Examples of the aromatic-aliphatic hydrocarbon group include $C_{7-9}$ phenylalkyl such as benzyl, phenethyl, 1-phenylethyl, 3-phenylpropyl, 2-phenylpropyl and 1-phenylpropyl; $C_{11-13}$ naphthylalkyl such as α-naphthylmethyl, α-naphthylethyl, β-naphthylmethyl, and β-naphthylethyl.

The aromatic hydrocarbon group is preferably a $C_{6-14}$ aromatic hydrocarbon group (e.g. aryl groups, etc.). Examples of the aromatic hydrocarbon group include phenyl and naphthyl (α-naphthyl, β-naphthyl).

Referring to the formula (I), examples of the heterocyclic group in a heterocyclic group that may be substituted for R is a 5- to 7-membered heterocyclic group containing 1 to 4 hetero-atoms selected from oxygen, sulfur, and nitrogen in addition to carbon as ring members or a condensed cyclic group. Examples of the condensed ring include one consisting of such a 5- to 7-membered heterocyclic group with a 6-membered ring containing 1 or 2 nitrogen atoms, a benzene ring, or a 5-membered ring containing one sulfur atom.

Examples of the heterocyclic group includes 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl, benzopyranyl and dihydrobenzopyranyl. The preferred heterocyclic group is pyridyl, oxazolyl or thiazolyl group.

Referring to the formula (I), the hydrocarbon group and heterocyclic group for R may respectively have 1 to 5, preferably 1 to 3 substituents at substitutable positions. Such substituents include for example aliphatic hydrocarbon groups, alicyclic hydrocarbon groups, aryl groups, aromatic heterocyclic groups, non-aromatic heterocyclic groups, halogen atom, nitro, amino group that may be substituted, acyl group that may be substituted, hydroxy group that may be substituted, thiol group that may be substituted, carboxyl group that may be esterified, amidino, carbamoyl, sulfamoyl, sulfo, cyano, azido, and nitroso.

Examples of the aliphatic hydrocarbon group include straight-chain or branched aliphatic hydrocarbon groups having 1 to 15 carbon atoms, such as alkyl groups, alkenyl groups, and alkynyl groups.

The preferred alkyl group is a $C_{1-10}$ alkyl group, such as methyl, ethyl, propyl, isopropyl, butyl, isobutyl, sec-butyl, t-butyl, pentyl, isopentyl, neopentyl, t-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, and decyl.

The preferred alkenyl group is a $C_{2-10}$ alkenyl group, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

The preferred alkynyl group is a $C_{2-10}$ alkynyl group, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

Examples of the alicyclic hydrocarbon group includes saturated or unsaturated alicyclic hydrocarbon groups having 3 to 12 carbon atoms, such as cycloalkyl groups cycloalkenyl groups, and cycloalkadienyl groups.

The preferred cycloalkyl group is a $C_{3-10}$ cycloalkyl group, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, and bicyclo[4.3.1]decyl.

The preferred cycloalkenyl group is a $C_{3-10}$ cycloalkenyl group, such as 2-cyclopenten-1-yl, 3-cyclopenten-1-yl, 2-cyclohexen-1-yl, and 3-cyclohexen-1-yl The preferred cycloalkadienyl group is a $C_{4-10}$ cycloalkadienyl group, such as 2,4-cyclopentadien-1-yl, 2,4-cyclohexadien-1-yl, and 2,5-cyclohexadien-1-yl.

The preferred aryl group is a $C_{6-14}$ aryl group, such as phenyl, naphthyl (1-naphthyl, 2-naphthyl), anthryl, phenanthryl, and acenaphthylenyl.

The preferred aromatic heterocyclic group includes monocyclic aromatic heterocyclic groups, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl; and condensed aromatic heterocyclic groups, such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

The preferred non-aromatic heterocyclic group includes oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, morpholino, and thiomorpholino.

Examples of the halogen atom include fluorine, chlorine, bromine, and iodine.

Referring to the amino group that may be substituted, examples of the substituted amino group include N-mono-substituted groups and N,N-di-substituted amino groups. Examples of the substituted amino group include amino groups having one or two substituents selected from the group consisting of $C_{1-10}$ alkyl groups, $C_{2-10}$ alkenyl groups, $C_{2-10}$ alkynyl groups, aromatic groups, heterocyclic groups or $C_{1-10}$ acyl groups (e.g. methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino, etc.).

Examples of the acyl group in the acyl groups that may be substituted include $C_{1-13}$ acyl groups, for example, $C_{1-10}$ alkanoyl groups, $C_{3-10}$ alkenoyl groups, $C_{4-10}$ cycloalkanoyl groups, $C_{4-10}$ cycloalkenoyl groups, $C_{6-12}$ aromatic carbonyl groups.

Preferred examples of the $C_{1-10}$ alkanoyl groups include formyl, acetyl, propionyl, butyryl, isobutyryl, valeryl, isovaleryl, pivaloyl, hexanoyl, heptanoyl, and octanoyl.

Preferred examples of the $C_{3-10}$ alkenoyl groups include acryloyl, methacryloyl, crotonoyl, and isocrotonoyl.

Preferred examples of the $C_{4-10}$ cycloalkanoyl groups include cyclobutanecarbonyl, cyclopentanecarbonyl, cyclohexanecarbonyl, and cycloheptanecarbonyl.

Preferred examples of the $C_{4-10}$ cycloalkenoyl groups include 2-cyclohexenecarbonyl.

Preferred examples of the $C_{6-12}$ aromatic carbonyl groups include benzoyl, naphthoyl, and nicotinoyl.

Examples of the substituents in the substituted acyl groups include $C_{1-3}$ alkyl groups, $C_{1-3}$ alkoxy groups, halogen atom (e.g. chlorine, fluorine, bromine, etc.), nitro, hydroxy, and amino.

Referring to the hydroxy group that may be substituted, examples of the substituted hydroxy includes alkoxy groups, cycloalkyloxy groups, alkenyloxy groups, cycloalkenyloxy groups, aralkyloxy groups, acyloxy groups, and aryloxy groups.

The preferred alkoxy group includes $C_{1-10}$ alkoxy groups, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, and nonyloxy.

The preferred cycloalkyloxy group includes $C_{3-10}$ cycloalkyloxy groups, such as cyclobutoxy, cyclopentyloxy, and cyclohexyloxy.

The preferred alkenyloxy group includes $C_{2-10}$ alkenyloxy groups, such as allyloxy, crotyloxy, 2-pentenyloxy, and 3-hexenyloxy.

The preferred cycloalkenyloxy group includes $C_{3-10}$ cycloalkenyloxy groups, such as 2-cyclopentenylmethoxy, and 2-cyclohexenylmethoxy.

The preferred aralkyloxy group includes $C_{7-10}$ aralkyloxy groups, such as phenyl-$C_{1-4}$ alkyloxy (e.g. benzyloxy, phenethyloxy, etc.).

The preferred acyloxy group includes $C_{2-13}$ acyloxy groups, more preferably $C_{2-4}$ alkanoyloxy groups (e.g. acetyloxy, propionyloxy, butyryloxy, isobutyryloxy, etc.).

The preferred aryloxy group includes $C_{6-14}$ aryloxy groups, such as phenoxy, and naphthyloxy. This aryloxy group may have 1 or 2 substituents. Examples of the substituents include halogen atom (e.g. chlorine, fluorine, bromine, etc.). Examples of the substituted aryloxy group includes 4-chlorophenoxy.

Referring to the thiol group that may be substituted, examples of the substituted thiol group include alkylthio groups, cycloalkylthio groups, alkenylthio groups, cycloalkenylthio groups, aralkylthio groups, acylthio groups, and arylthio groups.

The preferred alkylthio group includes $C_{1-10}$ alkylthio groups, such as methylthio, ethylthio, propylthio, isopropylthio, butylthio, isobutylthio, sec-butylthio, t-butylthio, pentylthio, isopentylthio, neopentylthio, hexylthio, heptylthio, and nonylthio.

The preferred cycloalkylthio group includes $C_{3-10}$ cycloalkylthio groups such as cyclobutylthio, cyclopentylthio, and cyclohexylthio.

The preferred alkenylthio group includes $C_{2-10}$ alkenylthio groups, such as allylthio, crotylthio, 2-entenylthio, and 3-hexenylthio.

The preferred cycloalkenylthio group includes $C_{3-10}$ cycloalkenylthio groups such as 2-cyclopentenylthio, and 2-cyclohexenylthio.

The preferred aralkylthio group includes $C_{7-10}$ aralkylthio groups, such as phenyl-$C_{1-4}$ alkylthio (e.g. benzylthio, phenethylthio, etc.).

The acylthio group is preferably a $C_{2-13}$ acylthio group, more preferably a $C_{2-4}$ alkanoylthio group (e.g. acetylthio, propionylthio, butyrylthio, isobutyrylthio, etc.).

The preferred arylthio group includes $C_{6-14}$ arylthio groups, such as phenylthio, and naphthylthio. This arylthio group may have 1 or 2 substituents. Examples of the substituents include halogen atom (e.g. chlorine, fluorine, bromine, etc.). Examples of the substituted arylthio group includes 4-chlorophenylthio.

The carboxyl group that may be esterified includes alkoxycarbonyl groups, aralkyloxycarbonyl groups, and aryloxycarbonyl groups.

The preferred alkoxycarbonyl group includes $C_{2-5}$ alkoxycarbonyl groups, such as methoxycarbonyl, ethoxycarbonyl, propoxycarbonyl, and butoxycarbonyl.

The preferred aralkyloxycarbonyl group includes $C_{8-10}$ aralkyloxycarbonyl groups, such as benzyloxycarbonyl.

The preferred aryloxycarbonyl group includes $C_{7-15}$ aryloxycarbonyl groups, such as phenoxycarbonyl, and p-tolyloxycarbonyl.

The preferred substituent on the hydrocarbon or heterocyclic group for R includes $C_{1-10}$ alkyl groups, aromatic heterocyclic groups, and $C_{6-14}$ aryl groups. Particularly preferred is $C_{1-3}$ alkyl, furyl, thienyl, phenyl, or naphthyl.

Referring to the formula (I), when the substituent on the hydrocarbon or heterocyclic group for R is an alicyclic hydrocarbon group, an aryl group, an aromatic heterocyclic group, or a non-aromatic heterocyclic group, this substituent may further have one or more, preferably 1 to 3 suitable substituents. Examples of such substituents include $C_{1-6}$ alkyl groups, $C_{2-6}$ alkenyl groups, $C_{2-6}$ alkynyl groups, $C_{3-7}$ cycloalkyl groups, $C_{6-14}$ aryl groups, aromatic heterocyclic groups (e.g. thienyl, furyl, pyridyl, oxazolyl, thiazolyl, etc.), non-aromatic heterocyclic groups (e.g. tetrahydrofuryl, morpholino, thiomorpholino, piperidino, pyrrolidino, piperazino, etc.), $C_{7-9}$ aralkyl groups, amino, N-mono-$C_{1-4}$ alkylamino groups, N,N-di-$C_{1-4}$ alkylamino groups, $C_{2-8}$ acylamino groups (e.g. acetylamino, propionylamino, benzoylamino, etc.), amidino, $C_{2-8}$ acyl groups (e.g. $C_{2-8}$ alkanoyl groups, etc.), carbamoyl, N-mono-$C_{1-4}$ alkylcarbamoyl groups, N,N-di-$C_{1-4}$ alkylcarbamoyl groups, sulfamoyl, N-mono-$C_{1-4}$ alkylsulfamoyl groups, N,N-di-$C_{1-4}$ alkylsulfamoyl groups, carboxyl, $C_{2-8}$ alkoxycarbonyl groups, hydroxy, $C_{1-4}$ alkoxy groups, $C_{2-5}$ alkenyloxy groups, $C_{3-7}$ cycloalkyloxy groups, $C_{7-9}$ aralkyloxy groups, $C_{6-14}$ aryloxy groups, mercapto, $C_{1-4}$ alkylthio groups, $C_{7-9}$ aralkylthio groups, $C_{6-14}$ arylthio groups, sulfo, cyano, azido, nitro, nitroso, and halogen atom.

In the formula (I), R is preferably a heterocyclic group that may be substituted. More preferably, R is pyridyl, oxazolyl, or thiazolyl group, which may have 1 to 3 substituents selected from the group consisting of $C_{1-3}$ alkyl, furyl, thienyl, phenyl, and naphthyl.

Referring to the formula (I), Y represents —CO—, —CH(OH)— or —NR³— where R³ represents an alkyl group that may be substituted. Preferred is —CH(OH)— or —NR³—. Examples of an alkyl group in the alkyl group that may be substituted for $R^3$, include $C_{1-4}$ alkyl groups, such as methyl, ethyl, propyl, isopropyl, butyl, isobutyl, sec-butyl, and t-butyl. Examples of the substituent include halogen atom (e.g. fluorine, chlorine, bromine, iodine), $C_{1-4}$ alkoxy groups (e.g. methoxy, ethoxy, propoxy, butoxy, isobutoxy, sec-butoxy, t-butoxy, etc.), hydroxy, nitro, and $C_{1-4}$ acyl groups (e.g. formyl, acetyl, propionyl, etc.).

The symbol m represents 0 or 1, and is preferably 0.

The symbol n represents 0, 1 or 2, and is preferably 0 or 1.

X represents CH or N, and is preferably CH.

Referring to the formula (I), A represents a chemical bond or a bivalent aliphatic hydrocarbon group having 1 to 7 carbon atoms. This aliphatic hydrocarbon group may be straight-chain or branched and may further be saturated or unsaturated. Thus, for example, —CH₂—, —CH(CH₃)—, —(CH₂)₂—, —CH(C₂H₅)—, (CH₂)₃—, —(CH₂)₄—, —(CH₂)₅—, —(CH₂)₆—, —(CH₂)₇ —, etc. can be mentioned for the saturated bivalent aliphatic hydrocarbon group, while —CH=CH—, —C(CH₃)=CH—, —CH=CH—CH₂—, —C(C₂H₅)=CH—, —CH₂—CH=CH—CH₂—, —CH₂—CH₂—CH=CH—CH₂—, —CH=CH—CH=CH—CH₂—, —CH=CH—CH=CH—CH=CH—CH₂—, etc. can be mentioned for the unsaturated bivalent aliphatic hydrocarbon group. A preferably represents a chemical bond or a bivalent aliphatic hydrocarbon group having 1 to 4 carbon atoms, which is preferably a saturated group. More preferably, A represents a chemical bond or —(CH₂)₂—.

The alkyl group for $R^1$ includes one similar to the alkyl group for the above-described $R^3$. $R^1$ is preferably hydrogen.

Referring to the formula (I), the partial structural formula:

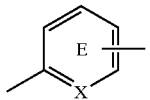 is preferably the formula: 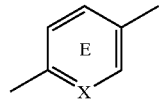

wherein each symbol has the same meanings as described above.

Furthermore, ring E may optionally have 1 to 4 substituents at substitutable positions. Examples of such substituents include an alkyl group, a hydroxy group that may be substituted, halogen atom, an acyl group that may be substituted, nitro, and an amino group that may be substituted. These substituents may be the same as the substituents mentioned for the hydrocarbon or heterocyclic group for the above-described R.

Ring E, namely the partial structural formula:

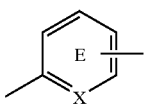 is preferably the formula: 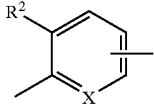

wherein R² represents hydrogen, an alkyl group, a hydroxy group that may be substituted, halogen atom, an acyl group that may be substituted, nitro, or an amino group that may be substituted.

The alkyl group, hydroxy group that may be substituted, halogen atom, acyl group that may be substituted, and amino group that may be substituted, for R², may each be the same as the substituents mentioned for the hydrocarbon or heterocyclic group for the above-described R. R² is preferably hydrogen, hydroxy group that may be substituted, or halogen atom. R² is more preferably hydrogen, or hydroxy group that may be substituted. Especially preferable is hydrogen or a $C_{1-4}$ alkoxy group.

Referring to the formula (I), L and M respectively represent hydrogen or may be combined with each other to form a chemical bond, and preferably they are hydrogen.

The compound in which L and M are combined with each other to form a chemical bond, may exist as (E)- and (Z)-isomers, owing to the double bond at 5-position of the azolidinedione ring.

The compound in which L and M respectively represent hydrogen, may exist as optical isomers, i.e. (R)- and (S)-forms, with respect to the asymmetric carbon at 5-position of the azolidinedione ring. This compound includes these optically active compounds, i.e. (R)- and (S)-forms, as well as the racemic form.

The preferred compound represented by the formula (I) includes the compound in which R represents pyridyl, oxazolyl, or thiazolyl group, optionally having 1 to 3 substituents selected from the group consisting of $C_{1-3}$ alkyl, furyl, thienyl, phenyl, and naphthyl; m is 0; n is 0 or 1; X represents CH; A represents a chemical bond or —$(CH_2)_2$—; R¹ represents hydrogen; ring E, namely the partial structural formula:

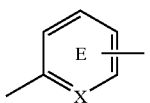 is the formula: 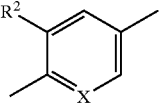

wherein R² is hydrogen or a $C_{1-4}$ alkoxy group; and L and M represent hydrogen.

Examples of the preferred compound represented by the formula (I) includes
5-[4-[2-(5-ethyl-2-pyridyl)ethoxy]benzyl]-2,4-thiazolidinedione (generic name: pioglitazone/AD-4833);
5-[[4-[(3,4-dihydro-6-hydroxy-2,5,7,8-tetramethyl-2H-1-benzopyran-2-yl)methoxy]phenyl]methyl]-2,4-thiazolidinedione (generic name: troglitazone/CS-045);
5-[[4-[2-(methyl-2-pyridinylamino)ethoxy]phenyl]methyl]-2,4-thiazolidinedione (generic name: rosiglitazone/BRL-49653); and
5-[3-[4-(5-methyl-2-phenyl-4-thiazolylmethoxy]phenyl]propyl]-2,4-oxazolidinedione.

An especially preferable compound represented by the formula (I) is pioglitazone.

A salt of a compound represented by the formula (I) includes a pharmacologically acceptable salt, such as salts with inorganic bases, salts with organic bases, salts with inorganic acids, salts with organic acids, and salts with basic or acidic amino acids.

The preferred salt with an inorganic base includes salts with alkali metal such as sodium, potassium, etc. or alkaline earth metal such as calcium, magnesium, etc.; aluminum salt, and ammonium salts.

The preferred salt with an organic base includes salts with trimethylamine, triethylamine, pyridine, picoline, ethanolamine, diethanolamine, triethanolamine, dicyclohexylamine, N,N-dibenzylethylenediamine, etc.

The preferred salt with an inorganic acid includes salts with hydrochloric acid, hydrobromic acid, nitric acid, sulfuric acid, phosphoric acid, etc.

The preferred salt with an organic acid includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

The preferred salt with a basic amino acid includes salts with arginine, lysine, ornithine, etc. The preferred salt with an acidic amino acid includes salts with aspartic acid, glutamic acid, etc.

A compound represented by the formula (I) or salt thereof is preferably pioglitazone hydrochloride, troglitazone or rosiglitazone (or its maleate), especially preferably pioglitazone hydrochloride.

A compound represented by the formula (I) or salt thereof can be produced in accordance with methods described in JP-A S55(1980)-22636 (EP-A-8203), JP-A S60(1985)-208980 (EP-A-155845), JP-A S61(1986)-286376 (EP-A-208420), JP-A S61(1986)-85372 (EP-A-177353), JP-A S61(1986)-267580 (EP-A-193256), JP-A H5(1993)-86057 (WO-A-92/18501), JP-A H7(1995)-82269 (EP-A-605228), JP-A H7(1995)-101945 (EP-A-612743), EP-A-643050, EP-A-710659, etc, or methods analogous thereto.

Examples of the insulin sensitizer employed in the present invention include, in addition to the above-described compounds,
4-[4-[2-(5-methyl-2-phenyloxazol-4-yl)ethoxy]benzyl] isoxazolidin-3,5-dione (JTT-501);
5-[[3,4-dihydro-2-(phenylmethyl)-2H-1-benzopyran-6-yl] methyl]-2,4-thiazolidinedione (generic name: englitazone);
5-[[4-[3-(5-methyl-2-phenyl-4-oxazolyl)-1-oxopropyl] phenyl]methyl]-2,4-thiazolidinedione (generic name: darglitazone/CP-86325);
5-[2-(5-methyl-2-phenyl-4-oxazolylmethyl)benzofuran-5-ylmethyl]-2,4-oxazolidinedione (CP-92768);
5-(2-naphthalenylsulfonyl)-2,4-thiazolidinedione (AY-31637);
4-[(2-naphthalenyl)methyl]-3H-1,2,3,5-oxathiadiazol-2-oxide (AY-30711);
5-[[6-(2-fluorobenzyloxy)-2-naphthyl]methyl]-2,4-thiazolidinedione (MCC-555);
[5-[(2,4-dioxothiazolidin-5-yl)methyl]-2-methoxy-N-[[4-(trifluoromethyl)phenyl]methyl]benzamido (AHG-255);
4-[1-(3,5,5,8,8-pentamethyl-5,6,7,8-tetrahydronaphthalen-2-yl)ethenyl]benzoic acid (LGD1069);
6-[1-(3,5,5,8,8-pentamethyl-5,6,7,8-tetrahydronaphthalen-2-yl)cyclopropyl]nicotinic acid (LG100268);
1,4-bis[4-[(3,5-dioxo-1,2,4-oxadizolidin-2-yl)methyl] phenoxy]-2-butene (YM-440);
bexarotene; GI-262570; DRF-2593; HQL-975; DN-108; CS-011; dexlipotam; INS-1; AR-H-0329242; CLX-0901; FK-614; KRP-297; CRE-16336; NN-2344; BM-13-1258; S-15261; KB-R-7785; DRF-2725; GW-2570; GW-2433; MXC-3255; L-746449; L-767827; L-783281; GW-409544; etc.

The above compounds can be used in the form of a salt. Such salt includes one similar to the salt of a compound represented by the formula (I) mentioned above.

Examples of the insulin sensitizer used in the present invention further includes a compound of the formula:

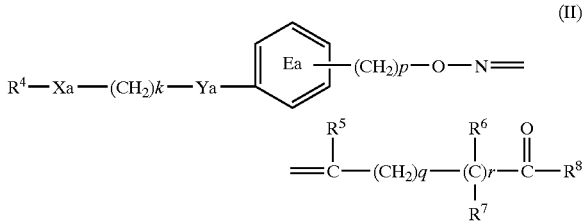

(II)

wherein $R^4$ represents a hydrocarbon group that may be substituted or a heterocyclic group that may be substituted; Xa represents a chemical bond, a group of the formula —CO—, —CH(OH)—, or —$NR^9$— where $R^9$ represents hydrogen or an alkyl group that may be substituted; k is an integer of 1 to 3; Ya represents oxygen atom, sulfur atom, —SO—, —$SO_2$—, or —$NR^{10}$ — where $R^{10}$ represents hydrogen or an alkyl group that may be substituted; ring Ea represents a benzene ring that may have further 1 to 3 substituents; p is an integer of 1 to 8; $R^5$ represents hydrogen, a hydrocarbon group that may be substituted, or a heterocyclic group that may be substituted; q is an integer of 0 to 6; r is 0 or 1; $R^8$ represents hydroxy, —$OR^{11}$ where $R^{11}$ represents a hydrocarbon group that may be substituted, or —$NR^{12}R^{13}$ where $R^{12}$ and $R^{13}$ are the same or different, and represent hydrogen, a hydrocarbon group that may be substituted, a heterocyclic group that may be substituted, or an acyl group that may be substituted, or $R^{12}$ and $R^{13}$ may be combined to form a ring; $R^6$ and $R^7$ are the same or different, and represent hydrogen or a hydrocarbon group that may be substituted, or $R^6$ and $R^5$ may be combined to form a ring; or a salt thereof, which is described in WO 99/58510.

Referring to the formula (II), "a hydrocarbon group that may be substituted or a heterocyclic group that may be substituted" for $R^4$ includes the same one mentioned for R in the formula (I).

$R^4$ is preferably a heterocyclic group that may be substituted, more preferably pyridyl, oxazolyl, thiazolyl, or triazolyl, each of which may be substituted. $R^4$ is especially preferably pyridyl, oxazolyl, thiazolyl, or triazolyl, each of which may have 1 or 2 substituents selected from the group consisting of $C_{1-3}$ alkyl, $C_{3-7}$ cycloalkyl, furyl, thienyl, phenyl, and naphthyl. Here, furyl, thienyl, phenyl, and naphthyl may have 1 or 2 substituents selected from the group consisting of $C_{1-3}$ alkyl, $C_{1-3}$ alkoxy, halogen (e.g. fluorine, chlorine, bromine, iodine, etc.), and $C_{1-3}$ haloalkyl.

Referring to the formula (II), "an alkyl group that may be substituted" for $R^9$ in the definition of Xa includes the same one mentioned for $R^3$ in the definition of Y in the formula (I).

Referring to the formula (II), k is an integer of 1 to 3, preferably 1 or 2.

Referring to the formula (II), Ya represents —O—, —S—, —SO—, —$SO_2$—, or —$NR^{10}$— where $R^{10}$ represents hydrogen or an alkyl group that may be substituted, with preference given to —O—, —S—, or —$NR^{10}$—. Here, "an alkyl group that may be substituted" for $R^{10}$ includes the same one mentioned for $R^3$ in the definition of Y in the formula (I).

Referring to the formula (II), the substituent in "a benzene ring that may have further 1 to 3 substituents" for ring Ea includes the same one mentioned as the substituent in ring E in the formula (I). The substituent is preferably $C_{1-4}$ alkyl group, $C_{1-4}$ alkoxy group or halogen atom.

Referring to the formula (II), p is preferably an integer of 1 to 3.

Referring to the formula (II), "a hydrocarbon group that may be substituted, or a heterocyclic group that may be substituted" for $R^5$ includes the same one mentioned for R in the formula (I).

$R^5$ is preferably a hydrocarbon group that may be substituted. $R^5$ is more preferably $C_{1-4}$ alkyl group, $C_{8-10}$ phenylalkenyl group, or $C_{6-14}$ aryl group, each of which may be substituted. Substituents which these hydrocarbon groups may have are preferably halogen atom, $C_{1-4}$ alkoxy group, $C_{6-14}$ aryloxy group, and aromatic heterocyclic group (e.g., furyl, thienyl).

Referring to the formula (II), q is preferably an integer of 0 to 4.

Referring to the formula (II), "a hydrocarbon group that may be substituted" for $R^{11}$ in the definition of $R^8$ includes the same one mentioned for R in the formula (I).

$R^{11}$ is preferably "$C_{1-4}$ alkyl group" and "$C_{6-10}$ aryl group (preferably phenyl) which may be substituted by $C_{1-4}$ alkyl group (preferably methyl, ethyl) or halogen atom (preferably chlorine)".

Referring to the formula (II), "a hydrocarbon group that may be substituted" and "a heterocyclic group that may be substituted" for $R^{12}$ and $R^{13}$ in the definition of $R^8$ include the same one mentioned for R in the formula (I).

As "an acyl group that may be substituted" for $R^{12}$ and $R^{13}$, employed is the same one mentioned for the substituent in R in the formula (I).

Examples of the ring formed by combination of $R^{12}$ and $R^{13}$ include 5 to 7 membered cyclic amino groups. Preferred are 1-pyrrolidinyl, 1-piperidinyl, 1-hexamethyleneiminyl, 4-morpholino, 4-thiomorpholino, etc.

Referring to the formula (II), "a hydrocarbon group that may be substituted" for $R^6$ and $R^7$ include the same one mentioned for R in the formula (I). Especially preferred is "an alkyl group that may be substituted" mentioned for $R^3$ in the definition of Y in the formula (I).

Examples of the ring formed by combination of $R^6$ and $R^5$ include $C_{5-11}$ cycloalkane and $C_{5-11}$ cycloalkene. Specifically mentioned are cyclopentane, cyclopentene, cyclohexane, cyclohexene, cycloheptane, cycloheptene, cyclooctane, cyclooctene, cyclononane, cyclononene, cyclodecane, cyclodecene, cycloundecane, cycloundecene, etc.

The compound represented by the formula (II) may exist as (E)-isomers and (Z)-isomers, owing to the imino bond. The compound includes (E)-isomers or (Z)-isomers alone, and mixtures thereof.

Preferred examples of the compound represented by the formula (II) include the following compounds (1) to (10):

(1) Z-2-[4-(5-methyl-2-phenyl-4-oxazolylmethoxy)benzyloxyimino]-2-phenylacetic acid;
(2) Z-4-[4-(5-methyl-2-phenyl-4-oxazolylmethoxy)benzyloxyimino]-4-phenylbutyric acid;
(3) Z-2-(4-bromophenyl)-2-[4-(5-methyl-2-phenyl-4-oxazolylmethoxy)benzyloxyimino]acetic acid;
(4) Z-2-[4-(5-methyl-2-phenyl-4-oxazolylmethoxy)benzyloxyimino]-2-(4-phenoxyphenyl)acetic acid;
(5) Z-4-(4-fluorophenyl )-4-[4-(5-methyl-2-phenyl-4-oxazolylmethoxy)benzyloxyimino]butyric acid;
(6) Z-3-methyl-2-[4-(5-methyl-2-phenyl-4-oxazolylmethoxy)benzyloxyimino]butyric acid;
(7) E-4-[4-(5-methyl-2-phenyl-4-oxazolylmethoxy)benzyloxyimino]-4-phenylbutyric acid;

(8) E-4-(4-fluorophenyl )-4-[4-(5-methyl-2-phenyl-4-oxazolylmethoxy)benzyloxyimino]butyric acid;

(9) E-4-[4-(5-methyl-2-phenyl-4-oxazolylmethoxy)benzyloxyimino]-4-phenylbutyramide;

(10) E-8-[4-(5-methyl-2-phenyl-4-oxazolylmethoxy)benzyloxyimino]-8-phenyloctanoic acid.

Hereafter, these compounds are also referred to simply as Compound (1), Compound (2) and the like.

The salt of the compound represented by the formula (II) includes the same as the salt of the compound represented by the formula (I). Especially preferred are sodium salt, potassium salt, hydrochloride, etc.

An insulin sensitizer is preferably pioglitazone hydrochloride, troglitazone, rosiglitazone (preferably its maleate), 4-[4-[2-(5-methyl-2-phenyloxazol-4-yl)ethoxy]benzyl]isoxazolidin-3,5-dione, or 5-[[6-(2-fluorobenzyloxy)-2-naphthyl]methyl]-2,4-thiazolidinedione. Especially preferred is pioglitazone hydrochloride.

An agent for improving ketosis or an agent for improving acidosis of the present invention may comprise two or more kinds of insulin sensitizers. Specific combinations when two kinds of insulin sensitizers are employed, include combinations of pioglitazone hydrochloride with one member selected from the group consisting of troglitazone, rosiglitazone (preferably its maleate), 4-[4-[2-(5-methyl-2-phenyloxazol-4-yl)ethoxy]benzyl]isoxazolidin-3,5-dione, 5-[[6-(2-fluorobenzyloxy)-2-naphthyl]methyl]-2,4-thiazolidinedione, 1,4-bis[4-[(3,5-dioxo-1,2,4-oxadizolidin-2-yl)methyl]phenoxy]-2-butene, bexarotene, GI-262570, DRF-2593, HQL-975 and DN-108.

A ketosis improving action is evaluated by, for instance, adding a test compound to "a system causing ketosis" and then determining changes in concentration of ketone bodies in this system.

For instance, diabetic ketosis is observed in a Wistar fatty rat which is an animal model of non-insulin dependent (type 2) diabetes mellitus. Therefore, a ketosis improving action of a test compound can be evaluated by comparing concentration of total ketone bodies in plasma between Wistar fatty rat groups with administration of a test compound (Experimental group) and Wistar fatty rat groups without administration of a test compound (Control group). The concentration of total ketone bodies in plasma means concentration of plasma ketone bodies such as acetoacetic acid, 3-hydroxybutyric acid, and etc., which can be determined in the following manner: [Determination method for concentration of total ketone bodies in plasma]

3-Hydroxybutyric acid (3-HB) in samples is specifically oxidized by 3-hydroxybutyric acid dehydrogenase (3-HBDH) in the presence of an oxidized form of β-thionicotinamide adenine dinucleotide (thio-NAD) to produce acetoacetic acid (AcAc) and a reduced form of β-thionicotinamide adenine dinucleotide (thio-NADH). On the other hand, AcAc is specifically reduced by 3-HBDH in the presence of a reduced form of β-nicotinamide adenine dinucleotide (NADH) to produce 3-HB and an oxidized form of β-nicotinamide adenine dinucleotide (NAD). The concentration of total ketone bodies which is the sum of 3-HB and AcAc in samples can be calculated by determining a production speed of thio-NADH thus obtained.

As described above, ketosis in the present invention includes diabetic ketosis. The diabetic ketosis means ketosis which is observed in patients suffering from diabetes (type 1 diabetes, type 2 diabetes, etc.).

A biguanide sometimes causes ketosis as shown in the experimental examples described hereafter. Ketosis in the present invention includes one caused by a biguanide.

An acidosis improving action is evaluated by, for instance, adding a test compound to "a system causing acidosis" and then determining changes in plasma pH in this system. Since these changes depend on changes in concentration of total ketone bodies or concentration of lactic acid in plasma, evaluation is also conducted by determining changes in these concentrations.

For instance, an acidosis improving action of a test compound can be evaluated indirectly by comparing concentration of total ketone bodies in plasma between Wistar fatty rat groups with administration of a test compound (Experimental group) and Wistar fatty rat groups without administration of a test compound (Control group) as described above.

As described above, acidosis in the present invention includes diabetic acidosis. The diabetic acidosis means acidosis which is observed in patients suffering from diabetes (type 1 diabetes, type 2 diabetes, etc.).

A biguanide sometimes causes acidosis. Acidosis in the present invention includes one caused by a biguanide.

An agent for improving ketosis or an agent for improving acidosis of the present invention can be an insulin sensitizer itself as an active ingredient. Usually, these agents can be produced by admixing the active ingredient with pharmaceutically acceptable carriers in accordance with per se known methods [conventional methods in fields of pharmaceutical manufacturing techniques, for instance, methods described in the Pharmacopoeia of Japan (e.g., Thirteenth Edition), etc.].

Examples of dosage forms of an agent for improving ketosis or an agent for improving acidosis of the present invention include oral dosage forms such as tablets, capsules (including soft capsules and microcapsules), powders, granules, syrups, and etc.; and non-oral dosage forms such as injections (e.g., subcutaneous injections, intravenous injections, intramuscular injections, intraperitoneal injections, etc.), external application forms (e.g., nasal spray preparations, transdermal preparations, ointments, etc.), suppositories (e.g., rectal suppositories, vaginal suppositories, etc.), pellets, drip infusions, and etc.

Methods of producing oral dosage forms and non-oral dosage forms are specifically explained below.

Oral dosage forms can be produced by adding to the active ingredient, for instance, an excipient (e.g., lactose, sucrose, starch, D-mannitol, xylitol, sorbitol, erythritol, crystalline cellulose, light silicic anhydride, etc.), a disintegrator (e.g., calcium carbonate, starch, carboxymethylcellulose, carboxymethylcellulose calcium, low-substituted hydroxypropylcellulose, croscarmellose sodium, carboxymethylstarch sodium, light silicic anhydride, etc.), a binder (e.g., α-starch, gum arabic, carboxymethylcellulose, hydroxypropylcellulose, hydroxypropylmethylcellulose, polyvinylpyrrolidone, crystalline cellulose, methylcellulose, sucrose, D-mannitol, trehalose, dextrin, etc.), or a lubricant (e.g., talc, magnesium stearate, calcium stearate, colloidal silica, polyethylene glycol 6000, etc.), and then compressing and molding the resulting mixture. To the oral dosage form, acids such as hydrochloric acid, phosphoric acid, malonic acid, succinic acid, DL-malic acid, tartaric acid, maleic acid, fumaric acid, citric acid, and etc.; or bases such as sodium carbonate, sodium hydrogencarbonate, sodium citrate, sodium tartrate, and etc. can be added for the purpose of promoting dissolution of the active ingredient.

The oral dosage forms can be coated, by the per se known method, for masking the taste or for enteric dissolution or sustained release. Examples of a coating material that can be employed includes, enteric coating polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose, etc.; gastric coating polymers such as polyvinylacetal diethylaminoacetate, aminoalkyl methacrylate copolymer E, etc.; water-soluble polymers such as hydroxypropylcellulose, hydroxypropylmethylcellulose, etc.; water-insoluble polymers such as ethylcellulose, aminoalkyl methacrylate copolymer RS, ethylacrylate-methylmethacrylate copolymer, etc.; wax, and etc. When coating is carried out, plasticizers such as polyethylene glycol, and etc.; and sunscreens such as titanium oxide, iron sesquioxide, and etc. can be employed together with the above coating material.

Injections can be produced by dissolving, suspending or emulsifying the active ingredient in an aqueous vehicle (e.g., distilled water, physiological saline, Ringer's solution, etc.) or an oily vehicle (e.g., vegetable oil such as olive oil, sesame oil, cottonseed oil, corn oil, etc.; or propylene glycol, macrogol, tricaprylin, etc.) together with a dispersant (e.g., Tween 80 (produced by Atlas Powder, U.S.A.), HCO 60 (produced by Nikko Chemicals, Japan), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, D-sorbitol, D-mannitol, xylitol, glucose, fructose, etc.) and etc.

If desired, also employed are additives such as a solubilizer (e.g., sodium salicylate, sodium acetate, polyethylene glycol, propylene glycol, D-mannitol, trehalose, benzyl benzoate, ethanol, trisaminomethane, cholesterol, triethanolamine, sodium carbonate, sodium citrate, etc.), a suspending agent (e.g., surfactants such as stearyltriethanolamine, sodium lauryl sulfate, laurylaminopropionic acid, lecithin, benzalkonium chloride, benzethonium chloride, glyceryl monostearate, and etc.; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose, and etc.), a buffering agent (e.g., buffer solutions such as phosphate, acetate, carbonate, citrate, and etc.), a stabilizer (e.g., human serum albumin, etc.), a soothing agent (e.g., propylene glycol, lidocaine hydrochloride, benzyl alcohol, etc.), an antiseptic (e.g., p-hydroxybenzoic acid esters, chlorobutanol, benzalkonium chloride, benzyl alcohol, phenethyl alcohol, dehydroacetic acid, sorbic acid, etc.) and etc.

External application forms can be produced by processing the active ingredient into a solid, semi-solid or liquid composition. For instance, a solid composition is produced by processing the active ingredient, either as such or in admixture with an excipient (e.g., lactose, D-mannitol, starch, microcrystalline cellulose, sucrose, etc.), a thickener (e.g., natural gums, cellulose derivatives, acrylic acid polymers, etc.), etc., into powders. The above liquid composition is produced in substantially the same manner as in the case of injections. The semi-solid composition is preferably provided in a hydrous or oily gel form or an ointment form. These compositions may optionally contain a pH control agent (e.g., phosphoric acid, citric acid, hydrochloric acid, sodium hydroxide, etc.), an antiseptic (e.g., p-hydroxybenzoic acid esters, chlorobutanol, benzalkonium chloride, benzyl alcohol, phenethyl alcohol, dehydroacetic acid, sorbic acid, etc.), and etc.

Suppositories can be produced by processing the active ingredient into an oily or aqueous composition, whether solid, semi-solid or liquid. Examples of oily bases that can be used in producing the composition include higher fatty acid glycerides [e.g., cacao butter, Witepsols (Huels Aktiengesellschaft, Germany), etc.], medium-chain fatty acid triglycerides [e.g., Miglyols (Huels Aktiengesellschaft, Germany), etc.], vegetable oils (e.g., sesame oil, soybean oil, cottonseed oil, etc.), etc. Examples of the aqueous bases include polyethylene glycols, propylene glycol, etc. Further, examples of the aqueous gel bases include natural gums, cellulose derivatives, vinyl polymers, and acrylic acid polymers, etc.

The contents of an insulin sensitizer in an agent for improving ketosis or an agent for improving acidosis of the present invention ranges, for instance, 0.1 to 100% by weight, preferably 5 to 80% by weight.

An agent for improving ketosis or an agent for improving acidosis of the present invention is low in toxicity, and can be safely used in mammals (e.g., human, mouse, rat, rabbit, dog, cat, bovine, equine, swine, monkey, etc.), either orally or non-orally.

The dosage of an agent for improving ketosis or an agent for improving acidosis of the present invention may be appropriately determined with reference to the dosage recommended for an insulin sensitizer as an active ingredient, and can be selected appropriately according to the subject, the age and body weight of the subject, current clinical status, administration time, dosage form, method of administration, and etc. The dosage of an insulin sensitizer can be selected appropriately based on clinically used dosage.

For administration of an agent for improving ketosis or an agent for improving acidosis to an adult (body weight: 50 kg), for instance, the dose per day is usually 0.01 to 1000 mg, preferably 0.1 to 600 mg of an insulin sensitizer which is an active ingredient. This dose can be administered once to several times a day.

Especially, when an agent for improving ketosis or an agent for improving acidosis which comprises pioglitazone hydrochloride as an insulin sensitizer is orally administered to an adult (body weight: 50 kg), the dose of the agent per day is usually 7.5 to 60 mg, preferably 15 to 45 mg of pioglitazone hydrochloride. This dose can be administered once to twice a day.

When an agent for improving ketosis or an agent for improving acidosis which comprises troglitazone of an insulin sensitizer is orally administered to an adult (body weight: 50 kg), the dose of the agent per day is usually 100 to 1000 mg, preferably 200 to 600 mg of troglitazone. This dose can be administered once to twice a day.

When an agent for improving ketosis or an agent for improving acidosis which comprises rosiglitazone (or its maleate) as an insulin sensitizer is orally administered to an adult (body weight: 50 kg), the dose of the agent per day is usually 1 to 12 mg, preferably 2 to 12 mg of rosiglitazone (or its maleate). This dose can be administered once to twice a day.

An agent for improving ketosis of the present invention can improve or treat ketosis observed in diseases showing ketosis, such as hepatic glycogenosis, endocrine diseases (e.g., hyperthyroidism, acromegaly, pheochromocytoma, glucagonoma), congenital metabolic disorders of carbohydrates or organic acids (e.g., fructose-bisphosphatase deficiency, methylmalonic acidemia, propionic acidemia, isovaleric acidemia, α-ketothiolase deficiency, lactacidemia), acetonemia vomiting or gastrointestinal diseases (e.g., diarrhea), and etc., and is employed as an agent for preventing or treating these diseases.

An agent for improving acidosis of the present invention can improve or treat acidosis observed in diseases showing acidosis, such as disturbance of consciousness, coma, respiratorydiseases (e.g., pulmonary tuberculosis), and etc., and is employed as an agent for preventing or treating these diseases.

In an agent for improving ketosis or an agent for improving acidosis of the present invention, a concomitant drug which does not affect a ketosis improving action or acidosis improving action of an insulin sensitizer, can be employed for the purpose of "reduction of the amount of an insulin sensitizer used", "reduction of side effect of an insulin sensitizer", and etc. Examples of the concomitant drug include "an antidiabetic agent other than an insulin sensitizer", "an agent for treating diabetic complications", "an agent for treating obesity", "an agent for treating hypertension", "an agent for treating hyperlipidemia", "a diuretic", and etc.

Further, a dietetic therapy (therapy by restriction of nutrition or calories) or a therapeutic exercise can be employed at the time of using an agent for improving ketosis or an agent for improving acidosis of the present invention, Examples of "an antidiabetic agent other than an insulin sensitizer" include insulin secretion enhancers, biguanides, insulin, α-glucosidase inhibitors, β3agonists, and etc.

Examples of the insulin secretion enhancers include sulfonylureas. Specific examples of the sulfonylureas include tolbutamide, chlorpropamide, tolazamide, acetohexamide, glyclopyramide or its ammonium salt, glibenclamide, gliclazide, 1-butyl-3-metanilylurea, carbutamide, glibornuride, glipizide, gliquidone, glisoxepid, glybuthiazole, glibuzole, glyhexamide, glymidine, glypinamide, phenbutamide, tolcyclamide, glimepiride, etc.

In addition to the above, examples of the insulin secretion enhancers include N-[[4-(1-methylethyl)cyclohexyl]carbonyl]-D-phenylalanine (Nateglinide, AY-4166), calcium (2S)-2-benzyl-3-(cis-hexahydro--2-isoindolinylcarbonyl)propionate dihydrate (Mitiglinide, KAD-1229), Repaglinide, GLP (Glucagon-like peptide)-1, GLP-1(7-36)-amide, V8-GLP-1 (LY-307161), Exendin-4 (AC-2993), DPP-728-A, V-411, JT-608, etc.

Examples of the biguanides include phenformin, metformin, buformin, etc.

Examples of the insulin include animal insulin extracted from bovine or porcine pancreas; semi-synthesized human insulin which is enzymatically synthesized from insulin extracted from porcine pancreas; and human insulin synthesized by genetic engineering techniques typically using *Escherichia coli* or yeasts; and etc. As insulin, also employed are insulin-zinc containing 0.45 to 0.9 (w/w) % of zinc; protamine-insulin-zinc produced from zinc chloride, protamine sulfate and insulin; and etc. Further, insulin may be its fragment or derivative (e.g., INS-1, etc.).

While insulin is available in a variety of types such as super immediate-acting, immediate-acting, bimodal-acting, intermediate-acting, long-acting, and etc., these types can be appropriately selected according to the patient's condition.

Examples of the α-glucosidase inhibitors include acarbose, voglibose, miglitol, emiglitate, etc.

Examples of the β3agonists include SR-58611-A, SB-226552, AZ40140, etc.

In addition to the above, examples of "an antidiabetic agent other than an insulin sensitizer" include ergoset, pramlintide, leptin, BAY-27-9955, T-1095, etc.

Examples of "an agent for treating diabetic complications" include aldose reductase inhibitors, glycation inhibitors, protein kinase C inhibitors, etc.

Examples of the aldose reductase inhibitors include, tolurestat; epalrestat; 3,4-dihydro-2,8-diisopropyl-3-thioxo-2H-1,4-benzoxazine-4-acetic acid; imirestat; zenarestat; 6-fluoro-2,3-dihydro-2',5'-dioxo-spiro[4H-1-benzopyran-4,4'-imidazolidine]-2-carboxamide (SNK-860); zopolrestat; sorbinil; 1-[(3-bromo-2-benzofuranyl)sulfonyl]-2,4-imidazolidinedione (M-16209); CT-112; NZ-314; ARI-509; etc.

Examples of the glycation inhibitors include pimagedine, etc.

Examples of the protein kinase C inhibitors include NGF, LY-333531, etc.

In addition to the above, examples of "an agent for treating diabetic complications" include alprostadil, thiapride hydrochloride, cilostazol, mexiletine hydrochloride, ethyl eicosapentaenoate, memantine, pimagedline (ALT-711), etc.

Examples of "an agent for treating obesity" include lipase inhibitors, anorectics, etc.

Examples of the lipase inhibitors include orlistat, etc.

Examples of the anorectics include dexfenfluramine, fluoxetine, sibutramine, baiamine, etc.

Examples of "an agent for treating hypertension" include angiotensin converting enzyme inhibitors, calcium antagonists, potassium channel openers, angiotensin II antagonists, etc.

Examples of the angiotensin converting enzyme inhibitors include captopril, enalapril, alacepril, delapril, ramipril, lisinopril, imidapril, benazepril, ceronapril, cilazapril, enalaprilat, fosinopril, moveltopril, perindopril, quinapril, spirapril, temocapril, trandolapril, manidipine, etc.

Examples of the calcium antagonists include nifedipine, amlodipine, efonidipine, nicardipine, etc.

Examples of the potassium channel openers include levcromakalim, L-27152, AL 0671, NIP-121, etc.

Examples of the angiotensin II antagonists include losartan, candesartan cilexetil, valsartan, irbesartan, (5-methyl-2-oxo-1,3-dioxoran-4-yl)methyl 4-(1-hydroxy-1-methylethyl)-2-propyl-1-[2'-(lH-tetrazol-5-yl)biphenyl-4-ylmethyl]imidazol-5-carboxylate (CS-866), E4177, etc.

Examples of "an agent for treating hyperlipidemia" include, HMG-CoA reductase inhibitors, fibrate compounds, etc.

Examples of the HMG-CoA reductase inhibitors include pravastatin, simvastatin, lovastatin, atorvastatin, fluvastatin, lipantil, cerivastatin, itavastatin, ZD-4522, or their salts (e.g., sodium salts, etc.), etc.

Examples of the fibrate compounds include bezafibrate, beclofibrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, etc.

Examples of "a diuretic" include xanthine derivative preparations, thiazide preparations, antialdosterone preparations, carbonate dehydratase inhibitors, chlorbenzenesulfonamide preparations, etc.

Examples of the xanthine derivative preparations include theobromine and sodium salicylate, theobromine and calcium salicylate, etc.

Examples of the thiazide preparations include ethiazide, cyclopenthiazide, trichlormethiazide, hydrochlorothiazide, hydroflumethiazide, benzylhydrochlorothiazide, penflutizide, polythiazide, methyclothiazide, etc.

Examples of the antialdosterone preparations include spironolactone, triamterene, etc.

Examples of the carbonate dehydratase inhibitors include acetazolamide, etc.

Examples of the chlorbenzenesulfonamide preparations include chlorthalidone, mefruside, indapamide, etc.

In addition to the above, examples of "a diuretic" include azosemide, isosorbide, ethacrynic acid, piretanide, bumetanide, furosemide, etc.

The above concomitant drugs can be used as a mixture of two or more kinds optionally selected. Examples of a specific combination when two kinds of concomitant drugs are used in combination include "combination of an insulin secretion enhancer and a biguanide", "combination of an insulin secretion enhancer and an α-glucosidase inhibitor", "combination of insulin and a biguanide", "combination of insulin and an α-glucosidase inhibitor", etc.

In case an agent for improving ketosis of the present invention is used to improve or treat diabetic ketosis, especially ketosis observed in patients suffering from type 1 diabetes, combination use of an insulin sensitizer with insulin is preferable.

In case an agent for improving acidosis of the present invention is used to improve or treat diabetic acidosis, especially acidosis observed in patients suffering from type 1 diabetes, combination use of an insulin sensitizer with insulin is preferable.

The timing of administrating an insulin sensitizer and a concomitant drug is not limited, and these can be administered to the subject at the same time or at staggered times.

The dosage of a concomitant drug may be determined based on clinically used dosage, and can be selected appropriately according to the subject, the age and body weight of the subject, current clinical status, administration time, dosage form, method of administration. combination, and etc.

The method for administrating a concomitant drug is not limited as long as an insulin sensitizer and a concomitant drug are combined at the time of administration. Examples of such methods include 1) administration of a single preparation prepared from an insulin sensitizer and a concomitant drug at the same time; 2) concomitant administration of two kinds of preparations prepared from an insulin sensitizer and a concomitant drug separately by the same administration route; 3) staggered administration of two kinds of preparations prepared from an insulin sensitizer and a concomitant drug separately by the same administration route; 4) concomitant administration of two kinds of preparations prepared from an insulin sensitizer and a concomitant drug separately by different administration routes; 5) staggered administration of two kinds of preparations prepared from an insulin sensitizer and a concomitant drug separately by different administration routes (e.g., administration of an insulin sensitizer and a concomitant drug in this order, or reverse order); and etc.

For administration of "an antidiabetic agent other than an insulin sensitizer" to an adult (body weight: 50 kg), for instance, the dose per day is usually 0.1 to 2500 mg, preferably 0.5 to 1000 mg. This dose can be administered once to several times a day.

For administration of insulin secretion enhancers to an adult (body weight: 50 kg), the dose per day is usually 0.1 to 1000 mg, preferably 1 to 100 mg. This dose can be administered once to several times a day.

For administration of biguanides to an adult (body weight: 50 kg), the dose per day is usually 10 to 2500 mg, preferably 100 to 1000 mg. This dose can be administered once to several times a day.

For administration (usually administration in the form of injections) of insulin to an adult (body weight: 50 kg), the dose per day is usually 10 to 100 U (Units), preferably 10 to 80 U (Units). This dose can be administered once to several times a day.

For administration of α-glucosidase inhibitors to an adult (body weight: 50 kg), the dose per day is usually 0.1 to 400 mg, preferably 0.6 to 300 mg. This dose can be administered once to several times a day.

For administration of β3agonists to an adult (body weight: 50 kg), the dose per day is usually 10 to 2000 mg, preferably 100 to 1000 mg. This dose can be administered once to several times a day.

For administration of "an agent for treating diabetic complications" to an adult (body weight: 50 kg), for instance, the dose per day is usually 0.1 to 2000 mg. This dose can be administered once to several times a day.

For administration of aldose reductase inhibitors to an adult (body weight: 50 kg), the dose per day is usually 1 to 1000 mg. This dose can be administered once to several times a day.

For administration of glycation inhibitors to an adult (body weight: 50 kg), the dose per day is usually 1 to 2000 mg. This dose can be administered once to several times a day.

For administration of protein kinase C inhibitors to an adult (body weight: 50 kg), the dose per day is usually 0.1 to 100 mg. This dose can be administered once to several times a day.

For administration of "an agent for treating obesity" to an adult (body weight: 50 kg), for instance, the dose per day is usually 0.01 to 1000 mg, preferably 0.1 to 1000 mg. This dose can be administered once to several times a day.

For administration of lipase inhibitors to an adult (body weight: 50 kg), the dose per day is usually 0.1 to 1000 mg. This dose can be administered once to several times a day.

For administration of anorectics to an adult (body weight: 50 kg), the dose per day is usually 0.01 to 1000 mg, preferably 0.1 to 500 mg. This dose can be administered once to several times a day.

For administration of "an agent for treating hypertension" to an adult (body weight: 50 kg), for instance, the dose per day is usually 0.01 to 1000 mg. This dose can be administered once to several times a day.

For administration of angiotensin converting enzyme inhibitors to an adult (body weight: 50 kg), the dose per day is usually 0.01 to 500 mg, preferably 0.1 to 100 mg. This dose can be administered once to several times a day.

For administration of calcium antagonists to an adult (body weight: 50 kg), the dose per day is usually 0.1 to 500 mg, preferably 1 to 200 mg. This dose can be administered once to several times a day.

For administration of potassium channel openers to an adult (body weight: 50 kg), the dose per day is usually 0.01 to 1000 mg. This dose can be administered once to several times a day.

For administration of angiotensin II antagonists to an adult (body weight: 50 kg), the dose per day is usually 0.1 to 500 mg, preferably 1 to 100 mg. This dose can be administered once to several times a day.

For administration of "an agent for treating hyperlipidemia" to an adult (body weight: 50 kg), for instance, the dose per day is usually 0.01 to 3000 mg, preferably 1 to 2000mg. This dose can be administered once to several times a day.

For administration of HMG-CoA reductase inhibitors to an adult (body weight: 50 kg), the dose per day is usually 0.01 to 100 mg, preferably 0.5 to 50 mg. This dose can be administered once to several times a day.

For administration of fibrate compounds to an adult (body weight: 50 kg), the dose per day is usually 1 to 2000 mg, preferably 10 to 1500 mg. This dose can be administered once to several times a day.

For administration of "a diuretic" to an adult (body weight: 50 kg), for instance, the dose per day is usually 0.01 mg to 100 g, preferably 0.05 mg to 10 g. This dose can be administered once to several times a day.

For administration of xanthine derivative preparations to an adult (body weight: 50 kg), the dose per day is usually 0.1 to 100 g, preferably 0.5 to 10 g. This dose can be administered once to several times a day.

For administration of thiazide preparations to an adult (body weight: 50 kg), the dose per day is usually 0.01 to 2000 mg, preferably 0.05 to 500 mg. This dose can be administered once to several times a day.

For administration of antialdosterone preparations to an adult (body weight: 50 kg), the dose per day is usually 1 to 2000 mg, preferably 10 to 1000 mg. This dose can be administered once to several times a day.

For administration of carbonate dehydratase inhibitors to an adult (body weight: 50 kg), the dose per day is usually 10 to 5000 mg, preferably 50 to 2000 mg. This dose can be administered once to several times a day.

For administration of chlorbenzenesulfonamide preparations to an adult (body weight: 50 kg), the dose per day is usually 1 to 2000 mg; preferably 10 to 1000 mg. This dose can be administered once to several times a day.

The proportion of an insulin sensitizer and a concomitant drug can be selected appropriately according to the subject, the age and body weight of the subject, current clinical status, administration time, dosage form, method of administration, and etc. For instance, a concomitant drug is used in a proportion of 0.0001 to 10000 weight parts relative to one weight part of an insulin sensitizer.

"An agent for preventing or treating hyperosmolar non-ketonic coma, infectious disease (e.g., respiratory infection, urinary tract infection, gastrointestinal tract infection, dermal soft tissue infection, inferior limb infection), diabetic osteoporosis, diabetic gangrene, xerostomia, lowered sense of hearing, angina pectoris, cerebrovascular disease or peripheral circulatory disturbance, which comprises an insulin sensitizer" of the present invention is low in toxicity, and can be safely used in mammals (e.g., human, mouse, rat, rabbit, dog, cat, bovine, equine, swine, monkey, etc.), either orally or non-orally.

The production method, dosage form, dosage, method of combination, and etc. are the same as in the case of the above-described agent for improving ketosis or agent for improving acidosis.

Further, in this agent the same concomitant drugs as those in the case of the above-described agent for improving ketosis or agent for improving acidosis can be used for the purpose of "reduction of the amount of an insulin sensitizer used", "reduction of side effect of an insulin sensitizer", and etc.

BEST MODE FOR CARRYING OUT THE INVENTION

The following Examples and Experimental Examples are intended to describe the present invention in further detail and should by no means be construed as limiting the scope of the invention.

EXAMPLE 1

A fluidized-bed granulating and drying machine (produced by Powerex) was charged with 2479.5 g of pioglitazone hydrochloride (2250 g in terms of pioglitazone), 13930.5 g of lactose and 540 g of carboxymethylcellulose calcium (carmellose calcium), followed by mixing at the preheating temperature and spraying 7500 g of an aqueous solution containing 450 g of hydroxypropylcellulose to yield granules. 16820 g of the granules were processed with cutter-mill (produced by Showa Kagaku Kikai Kousakusho) to yield milled granules. 16530 g of the milled granules, 513 g of carmellose calcium and 57 g of magnesium stearate were mixed to yield mixed powders by using a tumbling mixer (produced by Showa Kagaku Kikai Kousakusho). 16800 g of the mixed powders were tabletted by using a tabletting machine (produced by Kikusui Seisakusho) to yield 140000 tablets having the following composition and each containing 15 mg of pioglitazone.

| Composition per tablet (Unit: mg): | |
|---|---|
| 1) Pioglitazone hydrochloride | 16.53 |
| 2) Lactose | 92.87 |
| 3) Carmellose calcium | 7.2 |
| 4) Hydroxypropylcellulose | 3.0 |
| 5) Magnesium stearate | 0.4 |
| Total: | 120.0 |

EXAMPLE 2

In the similar manner to Example 1, 140000 tablets having the following composition and each containing 30 mg of pioglitazone were obtained.

| Composition per tablet (Unit: mg): | |
|---|---|
| 1) Pioglitazone hydrochloride | 33.06 |
| 2) Lactose | 76.34 |
| 3) Carmellose calcium | 7.2 |
| 4) Hydroxypropylcellulose | 3.0 |
| 5) Magnesium stearate | 0.4 |
| Total: | 120.0 |

EXAMPLE 3

In the similar manner to Example 2, 140000 tablets having the following composition and each containing 45 mg of pioglitazone were obtained.

| Composition per tablet (Unit: mg): | |
|---|---|
| 1) Pioglitazone hydrochloride | 49.59 |
| 2) Lactose | 114.51 |
| 3) Carmellose calcium | 10.8 |
| 4) Hydroxypropylcellulose | 4.5 |
| 5) Magnesium stearate | 0.6 |
| Total: | 180.0 |

Experimental Example 1

Effects of an insulin sensitizer (pioglitazone hydrochloride) on diabetic ketosis in Wistar fatty rats, animal models of non-insulin dependent diabetes mellitus (NIDDM), were studied.

First, Wistar fatty rats (31 week-old, male) were divided into two groups each consisting of 6 rats. One group was orally administered with pioglitazone hydrochloride (1 mg/kg body weight/day) suspended in a 0.5 (w/v) % aqueous methylcellulose solution, the other group with a 0.5 (w/v) % aqueous methylcellulose solution, respectively for 14 days. After administration, blood was collected from the tail vein of the Wistar fatty rats, and total ketone bodies in the plasma were enzymatically determined by using AutoWako total ketone bodies (Trade name)(Wako Pure Chemical Industries, Ltd., Japan) and Hitachi 7070 Autoanalyzing machine.

Wistar lean rats (6 rats), animal models of non diabetes mellitus (normal), were orally administered with a 0.5 (w/v) % aqueous methylcellulose solution for 14 days. Then, total ketone bodies in the plasma were determined in the same manner as above.

The results are shown in Table 1. In the table, W, lean, W. fatty and Pio mean Wistar lean rat, Wistar fatty rat and pioglitazone hydrochloride, respectively. Figures in the table represent means±standard deviation (number of subjects=6).

TABLE 1

| W. lean | 97.67 ± 23.18 $\mu$M |
|---|---|
| W. fatty without Pio | 170.23 ± 22.33 $\mu$M |
| W. fatty with Pio | 125.72 ± 12.49 $\mu$M* |

*p < 0.01 Dunnet's test v.s. Wistar fatty rat

As shown in Table 1, the concentration of total ketone bodies in Wistar lean rats, normal models, was 97.67±23.18 $\mu$M.

On the other hand, the concentration of total ketone bodies in Wistar fatty rats, NIDDM models, (groups without pioglitazone hydrochloride) was 170.23±22.33 $\mu$M, which was 72.56 $\mu$M higher as compared with Wistar lean rats, normal models.

The concentration of total ketone bodies in Wistar fatty rats, NIDDM models, (groups with pioglitazone hydrochloride) was 125.72±12.49 $\mu$M, which was 44.51 $\mu$M lower as compared with the group without pioglitazone hydrochloride.

The above results reveal that an insulin sensitizer (pioglitazone hydrochloride) improves diabetic ketosis.

Experimental Example 2

Effects of an insulin sensitizer (pioglitazone hydrochloride) on ketosis caused by a biguanide (metformin) in Wistar fatty rats, NIDDM models, were studied.

First, Wistar fatty rats (31 week-old, male) were divided into three groups, namely Groups A, B and C, each consisting of 6 rats. Group A was orally administered with a 0.5 (w/v) % aqueous methylcellulose solution, Group B with metformin (300 mg/kg body weight/day) suspended in a 0.5 (w/v) % aqueous methylcellulose solution, Group C with metformin (300 mg/kg body weight/day) suspended in a 0.5 (w/v) % aqueous methylcellulose solution and pioglitazone hydrochloride (1 mg/kg body weight/day) suspended in a 0.5 (w/v) % aqueous methylcellulose solution, respectively for 14 days. After administration, blood was collected from the tail vein of the Wistar fatty rats, and total ketone bodies in the plasma were determined in the same manner as in Experimental Example 1.

The results are shown in Table 2. In the table, W. fatty. Met and Pio mean Wistar fatty rat, metformin and pioglitazone hydrochloride, respectively. Figures in the table represent means±standard deviation (number of subjects=6).

TABLE 2

| Group A: | |
|---|---|
| W. fatty without Met and Pio | 170.23 ± 22.33 $\mu$M |
| Group B: | |
| W. fatty with Met | 182.00 ± 22.50 $\mu$M |
| Group C: | |
| W. fatty with Met and Pio | 155.25 ± 42.12 $\mu$M |

As shown in Table 2, the concentration of total ketone bodies in a group without metformin and pioglitazone hydrochloride (Group A) was 170.23±22.33 $\mu$M.

On the other hand, the concentration of total ketone bodies in a group with metformin (Group B) was 182.00±22.50 $\mu$M, which was 11.77 $\mu$M higher as compared with the group without metformin and pioglitazone hydrochloride (Group A).

The concentration of total ketone bodies in a group with metformin and pioglitazone hydrochloride (Group C) was 155.25±42.12 $\rho$M, which was 26.75 $\mu$M lower as compared with the group with metformin (Group B).

Experimental Example 3

The concentration of total ketone bodies in plasma of Wistar fatty rats was determined in the same manner as in Experimental Example 2 except that the administration period was changed from 14 days to 7 days.

The results are shown in Table 3. In the table, W. fatty. Met and Pio mean Wistar fatty rat, metformin and pioglitazone hydrochloride, respectively. Figures in the table represent means±standard deviation (number of subjects=6).

TABLE 3

| Group A: | |
|---|---|
| W. fatty without Met and Pio | 160.37 ± 14.00 $\mu$M |
| Group B: | |
| W. fatty with Met | 199.23 ± 55.69 $\mu$M |
| Group C: | |
| W. fatty with Met and Pio | 153.50 ± 26.14 $\mu$M |

As shown in Table 3, the concentration of total ketone bodies in a group without metformin and pioglitazone hydrochloride (Group A) was 160.37±14.00 $\mu$M.

On the other hand, the concentration of total ketone bodies in a group with metformin (Group B) was 199.23±55.69 $\mu$M, which was 38.86 $\mu$M higher as compared with the group without metformin and pioglitazone hydrochloride (Group A).

The concentration of total ketone bodies in a group with metformin and pioglitazone hydrochloride (Group C) was 153.50±26.14 $\mu$M, which was 45.73 $\mu$M lower as compared with the group with metformin (Group B).

The above results in Experimental Examples 2 and 3 reveal that an insulin sensitizer (pioglitazone hydrochloride) improves ketosis caused by a biguanide (metformin). Further, the above results in Experimental Examples 2 and 3 reveal that an insulin sensitizer (pioglitazone hydrochloride) also improves ketosis caused by diabetes as well as ketosis caused by a biguanide (metformin).

Industrial Applicability

An agent for improving ketosis of the present invention is low in toxicity and useful as an agent for preventing or treating diseases showing ketosis, such as hepatic glycogenosis, endocrine diseases (e.g., hyperthyroidism, acromegaly, pheochromocytoma, glucagonoma), congenital metabolic disorders of carbohydrates or organic acids (e.g., fructose-bisphosphatase deficiency, methylmalonic acidemia, propionic acidemia, isovaleric acidemia, β-ketothiolase deficiency, lactacidemia), acetonemia vomiting or gastrointestinal diseases (e.g., diarrhea).

An agent for improving acidosis of the present invention is low in toxicity and useful as an agent for preventing or treating diseases showing acidosis, such as disturbance of consciousness, coma, respiratory diseases (e.g., pulmonary tuberculosis).

What is claimed is:

1. A method for improving or treating ketosis in a mammal in need thereof, which comprises administering to said mammal an effective amount of an insulin sensitizer selected from the group consisting of
  1) pioglitazone or a salt thereof,
  2) a compound of the formula:

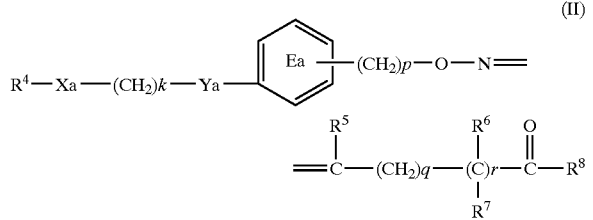

(II)

wherein $R^4$ represents a hydrocarbon group that may be substituted or a heterocyclic group that may be substituted; Xa represents a chemical bond, a group of the formula —CO—, —CH(OH)—, or —NR$^9$— where $R^9$ represents hydrogen or an alkyl group that may be substituted; k is an integer of 1 to 3; Ya represents oxygen atom, sulfur atom, —SO—, —SO$_2$—, or —NR$^{10}$— where $R^{10}$ represents hydrogen or an alkyl group that may be substituted; ring Ea represents a benzene ring that may have further 1 to 3 substituents; p is an integer of 1 to 8; $R^5$ represents hydrogen, a hydrocarbon group that may be substituted, or a heterocyclic group that may be substituted; q is an integer of 0 to 6; r is 0 or 1; $R^8$ represents hydroxy, —OR$^{11}$ where $R^{11}$ represents a hydrocarbon group that may be substituted, or —NR$^{12}$R$^{13}$ where $R^{12}$ and $R^{13}$ are the same or different, and represent hydrogen, a hydrocarbon group that may be substituted, a heterocyclic group that may be substituted, or an acyl group that may be substituted, or $R^{12}$ and $R^{13}$ may be combined to form a ring; $R^6$ and $R^7$ are the same or different, and represent hydrogen or a hydrocarbon group that may be substituted, or $R^6$ and $R^5$ may be combined to form a ring; or a salt thereof;

3) 5-[[6-(2-fluorobenzyloxy)-2-naphthyl]methyl]-2,4-thiazolidinedione;
  4) FK-614; and
  5) KRP-297.

2. The method of claim 1 wherein the insulin sensitizer is pioglitazone hydrochloride.

3. The method of claim 1 wherein the ketosis is diabetic ketosis.

4. The method of claim 1 which is for treating hepatic glycogenosis, endocrine diseases, congenital metabolic disorders of carbohydrates or organic acids, acetonemia, vomiting or gastrointestinal diseases.

5. The method of claim 1 wherein the insulin sensitizer is a compound of the formula:

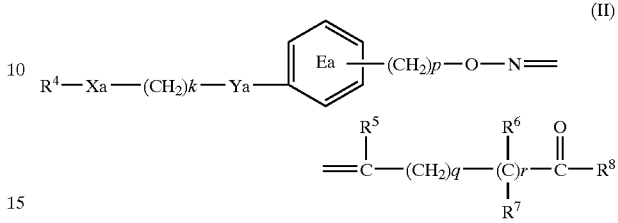

(II)

wherein $R^4$ represents a hydrocarbon group that may be substituted or a heterocyclic group that may be substituted; Xa represents a chemical bond, a group of the formula —CO—, —CH(OH)—, or —NR$^9$— where $R^9$ represents hydrogen or an alkyl group that may be substituted; k is an integer of 1 to 3; Ya represents oxygen atom, sulfur atom, —SO—, —SO$_2$—, or —NR$^{10}$— where $R^{10}$ represents hydrogen or an alkyl group that may be substituted; ring Ea represents a benzene ring that may have further 1 to 3 substituents; p is an integer of 1 to 8; $R^5$ represents hydrogen, a hydrocarbon group that may be substituted, or a heterocyclic group that may be substituted; q is an integer of 0 to 6; r is 0 or 1; $R^8$ represents hydroxy, —OR$^{11}$ where $R^{11}$ represents a hydrocarbon group that may be substituted, or —NR$^{12}$R$^{13}$ where $R^{12}$ and $R^{13}$ are the same or different, and represent hydrogen, a hydrocarbon group that may be substituted, a heterocyclic group that may be substituted, or an acyl group that may be substituted, or $R^{12}$ and $R^{13}$ may be combined to form a ring; $R^6$ and $R^7$ are the same or different, and represent hydrogen or a hydrocarbon group that may be substituted, or $R^6$ and $R^5$ may be combined to form a ring; or a salt thereof.

6. The method of claim 5, wherein the compound is
  Z-2-[4-(5-methyl-2-phenyl-4-oxazolylmethoxy)benzyloxyimino]-2-phenylacetic acid;
  Z-4-[4-(5-methyl-2-phenyl-4-oxazolylmethoxy)benzyloxyimino]-4-phenylbutyric acid;
  Z-2-(4-bromophenyl)-2-[4-(5-methyl-2-phenyl-4-oxazolylmethoxy)benzyloxyimino]acetic acid;
  Z-2-[4-(5-methyl-2-phenyl-4-oxazolylmethoxy)benzyloxyimino]-2-(4-phenoxyphenyl)acetic acid;
  Z-4-(4-fluorophenyl )-4-[4-(5-methyl-2-phenyl-4-oxazolylmethoxy)benzyloxyimino]butyric acid;
  Z-3-methyl-2-[4-(5-methyl -2-phenyl-4-oxazolylmethoxy)benzyloxyimino]butyric acid;
  E-4-[4-(5-methyl-2-phenyl-4-oxazolylmethoxy)benzyloxyimino]-4-phenylbutyric acid;
  E-4-(4-fluorophenyl )-4-[4-(5-methyl-2-phenyl-4-oxazolylmethoxy)benzyloxyimino]butyric acid;
  E-4-[4-(5-methyl-2-phenyl-4-oxazolylmethoxy)benzyloxyimino]-4-phenylbutyramide; or
  E-8-[4-(5-methyl-2-phenyl-4-oxazolylmethoxy)benzyloxyimino]-8-phenyloctanoic acid.

7. The method of claim 1 wherein said ketosis is caused by a biguanide.

8. The method of claim 1 further comprising administering insulin to said mammal.

9. A method for improving or treating ketosis which comprises administering an effective amount of an insulin sensitizer in combination with insulin to a mammal in need thereof.

10. The method of claim 9 wherein the insulin sensitizer is selected from the group consisting of
1) pioglitazone or a salt thereof,
2) a compound of the formula:

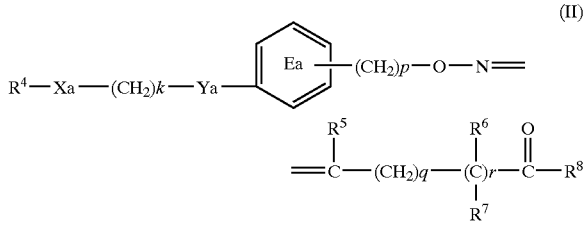

(II)

wherein $R^4$ represents a hydrocarbon group that may be substituted or a heterocyclic group that may be substituted; Xa represents a chemical bond, a group of the formula —CO—, —CH(OH)—, or —$NR^9$— where $R^9$ represents hydrogen or an alkyl group that may be substituted; k is an integer of 1 to 3; Ya represents oxygen atom, sulfur atom, —SO—, —$SO_2$—, or —$NR^{10}$— where $R^{10}$ represents hydrogen or an alkyl group that may be substituted; ring Ea represents a benzene ring that may have further 1 to 3 substituents; p is an integer of 1 to 8; $R^5$ represents hydrogen, a hydrocarbon group that may be substituted, or a heterocyclic group that may be substituted; q is an integer of 0 to 6; r is 0 or 1; $R^8$ represents hydroxy, —$OR^{11}$ where $R^{11}$ represents a hydrocarbon group that may be substituted, or —$NR^{12}R^{13}$ where $R^{12}$ and $R^{13}$ are the same or different, and represent hydrogen, a hydrocarbon group that may be substituted, a heterocyclic group that may be substituted, or an acyl group that may be substituted, or $R^{12}$ and $R^{13}$ may be combined to form a ring; $R^6$ and $R^7$ are the same or different, and represent hydrogen or a hydrocarbon group that may be substituted, or $R^6$ and $R^5$ may be combined to form a ring; or a salt thereof;

3) 5-[[6-(2-fluorobenzyloxy)-2-naphthyl]methyl]-2,4-thiazolidinedione;
4) FK-614; and
5) KRP-297.

11. The method of claim 10 wherein the insulin sensitizer is pioglitazone hydrochloride.

12. The method of claim 10, wherein the insulin sensitizer is a compound of the formula:

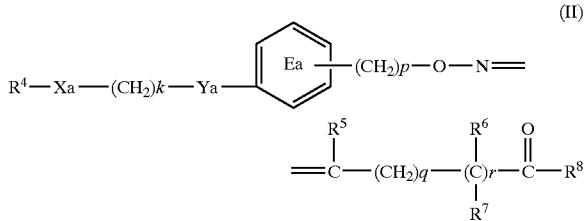

(II)

wherein $R^4$ represents a hydrocarbon group that may be substituted or a heterocyclic group that may be substituted; Xa represents a chemical bond, a group of the formula —CO—, —CH(OH)—, or —$NR^9$— where $R^9$ represents hydrogen or an alkyl group that may be substituted; k is an integer of 1 to 3; Ya represents oxygen atom, sulfur atom, —SO—, —$SO_2$—, or —$NR^{10}$— where $R^{10}$ represents hydrogen or an alkyl group that may be substituted; ring Ea represents a benzene ring that may have further 1 to 3 substituents; p is an integer of 1 to 8; $R^5$ represents hydrogen, a hydrocarbon group that may be substituted, or a heterocyclic group that may be substituted; q is an integer of 0 to 6; r is 0 or 1; $R^8$ represents hydroxy, —$OR^{11}$ where $R^{11}$ represents a hydrocarbon group that may be substituted, or —$NR^{12}R^{13}$ where $R^{12}$ and $R^{13}$ are the same or different, and represent hydrogen, a hydrocarbon group that may be substituted, a heterocyclic group that may be substituted, or an acyl group that may be substituted, or $R^{12}$ and $R^{13}$ may be combined to form a ring; $R^6$ and $R^7$ are the same or different, and represent hydrogen or a hydrocarbon group that may be substituted, or $R^6$ and $R^5$ may be combined to form a ring; or a salt thereof.

13. The method of claim 12 wherein the compound is

Z-2-[4-(5-methyl-2-phenyl-4-oxazolylmethoxy)benzyloxyimino]-2-phenylacetic acid;

Z-4-[4-(5-methyl-2-phenyl-4-oxazolylmethoxy)benzyloxyimino]-4-phenylbutyric acid;

Z-2-(4-bromophenyl)-2-[4-(5-methyl-2-phenyl-4-oxazolylmethoxy)benzyloxyimino]acetic acid;

Z-2-[4-(5-methyl-2-phenyl-4-oxazolylmethoxy)benzyloxyimino]-2-(4-phenoxyphenyl)acetic acid;

Z-4-(4-fluorophenyl)-4-[4-(5-methyl-2-phenyl-4-oxazolylmethoxy)benzyloxyimino]butyric acid;

Z-3-methyl-2-[4-(5-methyl-2-phenyl-4-oxazolylmethoxy)benzyloxyimino]butyric acid;

E-4-[4-(5-methyl-2-phenyl-4-oxazolylmethoxy)benzyloxyimino]-4-phenylbutyric acid;

E-4-(4-fluorophenyl)-4-[4-(5-methyl-2-phenyl-4-oxazolylmethoxy)benzyloxyimino]butyric acid;

E-4-[4-(5-methyl-2-phenyl-4-oxazolylmethoxy)benzyloxyimino]-4-phenylbutyramide; or E-8-[4-(5-methyl-2-phenyl-4-oxazolylmethoxy)benzyloxyimino]-8-phenyloctanoic acid.

14. The method of claim 9 wherein the ketosis is diabetic ketosis.

15. The method of claim 9 wherein said ketosis is caused by a biguanide.

16. The method of claim 9 which is for treating hepatic glycogenosis, endocrine diseases, congenital metabolic disorders of carbohydrates or organic acids, acetonemia, vomiting or gastrointestinal diseases.

* * * * *